(12) United States Patent
Eagan et al.

(10) Patent No.: US 6,658,282 B1
(45) Date of Patent: Dec. 2, 2003

(54) IMAGE REGISTRATION SYSTEM AND METHOD

(75) Inventors: Barry Eagan, Salt Lake City, UT (US); Lloyd M. Caldwell, Salt Lake City, UT (US); D. Robert Cady, MillCreek Township, UT (US); Donald C. Grove, Layton, UT (US); Gregg D. Niven, Kaysville, UT (US); Xan Nguyen, Salt Lake City, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 4 days.

(21) Appl. No.: 10/325,791

(22) Filed: Dec. 19, 2002

(51) Int. Cl.$^7$ .................................................. A61B 6/00
(52) U.S. Cl. ......................... 600/476; 600/407; 356/2; 606/10
(58) Field of Search ................................ 600/476, 407; 606/10, 12, 5; 356/2

(56) References Cited

U.S. PATENT DOCUMENTS

| | | | | | |
|---|---|---|---|---|---|
| 4,792,698 | A | * | 12/1988 | Pryor | 250/559.23 |
| 5,980,513 | A | * | 11/1999 | Frey et al. | 606/10 |
| 6,315,773 | B1 | * | 11/2001 | Frey et al. | 606/12 |

* cited by examiner

Primary Examiner—Marvin M. Lateef
Assistant Examiner—Barry Pass
(74) Attorney, Agent, or Firm—William Greener

(57) ABSTRACT

An apparatus for registering a series of video images of a spherical or quasi-spherical surface subject to movement relies on projecting at least four diffusely scattering spots of light on the surface in a preferred angular manner, and monitoring the movement of images of the light spots relative to a reference image of the light spots.

33 Claims, 5 Drawing Sheets

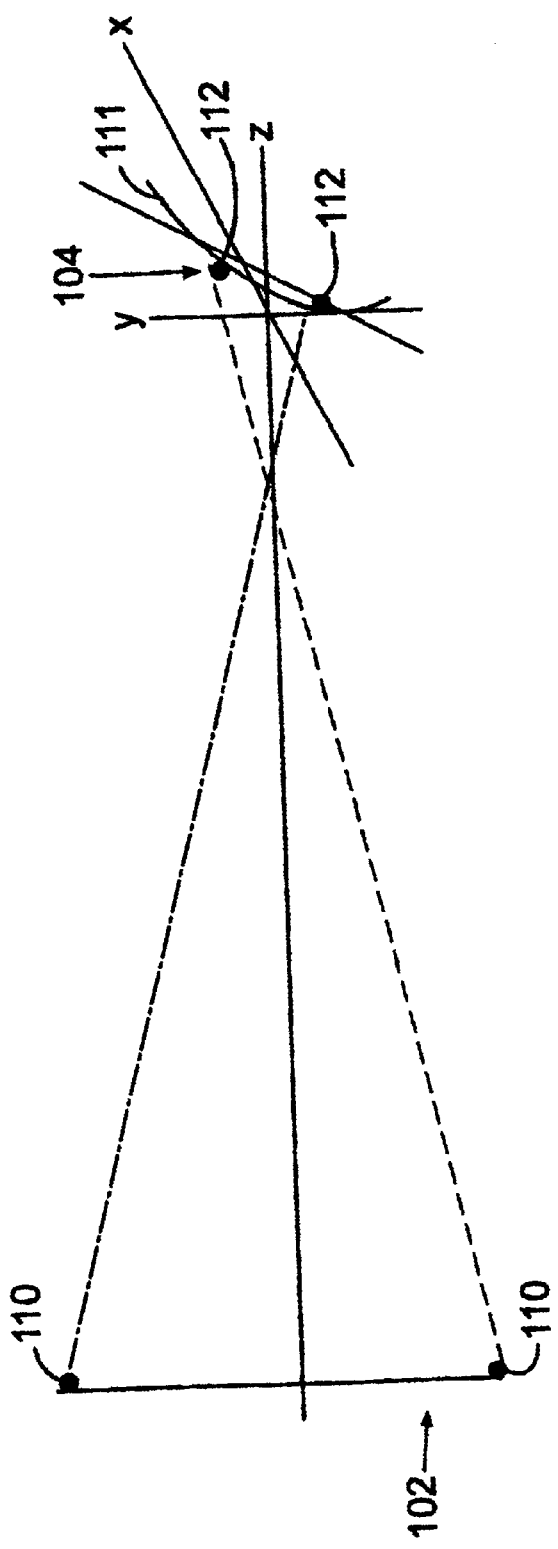

IMAGE REGISTRATION SYSTEM AND METHOD

BACKGROUND OF THE INVENTION

1. Field of the Invention

The invention is generally directed towards diagnostic image processing, and, more particularly to a device and system for position and motion sensing of a spherical object surface, and to a method for detecting such motion and registering a series of temporal image frames of the object surface.

2. Description of Related Art

The first step in any ophthalmic procedure is to diagnose the pathology of the eye and/or characterize its structure. In the field of refractive surgery for correcting defective vision of a person's eye, it is important to gather accurate information about the topography and pachymetry of the eye as well as the nature and magnitude of the aberrations that cause poor vision. The gathering of this diagnostic information typically requires the patient to engage some type of instrument and steadily view a target while the diagnostic information is acquired, usually through multiple video images taken over a time interval ranging from fractions of–to several seconds. This is a relatively long time frame in relation to the saccadic movement of the eye and the time it takes for a person to change their gaze during a measurement sequence. Voluntary or involuntary eye motion may cause a particular measurement parameter to be inaccurately recorded and a resulting vision correction application to be less than optimal.

In light of this, the inventors have recognized a need for a way to compensate for eye motion during the diagnostic procedure. Although the invention will be described with reference to monitoring and compensating for motion of a patient's eye, it will be appreciated that the apparatus and methods disclosed herein will apply to the monitoring and compensating of motion of any object having a spherical or quasi spherical object surface.

SUMMARY OF THE INVENTION

An embodiment of the invention is directed to a device for monitoring the spatial position of, and tracking the movement of, an object having a spherical or quasi spherical surface. The preferable object is the cornea of a person's eye. The device includes a projection component that employs at least one light-emitting element for projecting at least four spots of light onto the surface where at least two of the spots on the surface must not lie in the same plane. In addition, an image capture component captures a series of real-time video frames of the image of the object surface and the light spots illuminated on the surface. A computing component operates in conjunction with the image capture component and receives the images from the image capture component, locates each illumination light spot in each image frame, and determines a relationship between the image spots in each image frame. The device will preferably have four light-emitting elements that project four corresponding light spots onto the surface; and more preferably will include six light-emitting elements that illuminate portions of the surface with six corresponding light spots. According to a preferred aspect of a device embodiment of the invention, a banking/switching component is used in conjunction with six light-emitting elements and allows four of the six light-emitting elements to form light spots on the corneal surface at any given instant. This is useful when a competing light source is used in a particular application, for example, a scanned slit of light to measure corneal pachymetry. Applications that do not use a competing light source, for example, optical coherence tomography (OCT) and B/C scan require only four light spots. The type of light source is not critical and may include sources such as laser diodes, super luminescent diodes with associated focussing optics, or an incandescent light source with an optical accompaniment that will allow the light source to be focussed on the surface of the object, for example. The light sources are positioned in a planar arrangement with the plane normal to a reference axis of the object surface which, for the purpose of clarity of description, is preferably the optical axis of the cornea of the eye being monitored. Each of the light sources is aimed at the cornea of the subject eye in a pattern that is anywhere from about ½ to ⅔ of the distance from the center of the eye to the limbal boundary. This projection pattern allows the center of the cornea to remain free of light scatter which could be important if one wants to view the center of the cornea or view through the iris of the subject eye. Each of the light beams forming a light spot on the object surface diffusely scatters when striking the cornea due to the fragmented cell structure of the cornea. This scatter is seen as small, diffuse dots of light on the surface of the cornea. The relationship of the spots to one another is imaged, and then captured during each video frame of the diagnostic procedure. It is this relationship of the spots that allows the motion of the eye to be tracked in space.

The center of the sphere in space can be mathematically determined by four non-collinear points if each is defined in all three axes, x, y, and z. These four points will define the surface of the sphere. If a sphere can be determined by the location of these points, and four points of light are provided and compared to a reference, then the relative location of the sphere can be determined. Thus, a control image is established according to the invention for such a comparison. When the image of the sphere with the four incident light beams is captured by the imaging device and the resultant image is processed to locate the spots, comparison between sequential image spots yields spot location differences, capturing the amplitude and direction of patient eye motion with each frame. As each image is captured and the spots identified, a compensation vector for each image in the temporal sequence of image frames is constructed. If the object moves forward, between images, the spots in the subsequent image will be spread further apart. If the object moves up or down, or left or right, the spots will move asymmetrically in relation to the motion.

After the image capture system captures these images, they are sent to a computing device. The computing device locates each spot on each image. It then compares what the motion of each of the spots is in each frame and allows the images to be scaled, rotated, and moved in order to be reassembled accurately. The compensation vector is constructed and utilized to logically shift each frame into a uniform central frame of reference thus compensating for any motion of the source during the video image capture process. The computing device reassembles the images while compensating for the movement changes and allows the images to be re-registered with respect to one another with each spherical surface being concentric on the center. This allows motion compensation along all three axis.

The invention provides distinct advantages over a collinear tracking system. For example, the compensation vector is quick to generate once the light scatter spots are identified on the surface image. The methodology according to the invention is unique, numerical, and easily verified.

Since the light spots are not collinear, each image will be unique to the eye that was captured. The invention does not rely on light reflection to indicate motion, thus a poorly reflecting cornea can easily be tracked.

These and other advantages and objects of the present invention will become more readily apparent from the detailed description to follow. However, it should be understood that the detailed description and specific examples, while indicating the preferred embodiments of the invention, are given by way of illustration only, since various changes and modifications within the spirit and scope of the invention will become apparent to those skilled in the art based upon the description and drawings herein and the appended claims.

BRIEF DESCRIPTION OF THE DRAWINGS

FIG. 2a is a side view illustration of the extremum light projection path according to an embodiment of the invention;

DETAILED DESCRIPTION OF A PREFERRED EMBODIMENT OF THE INVENTION

Figure 1:
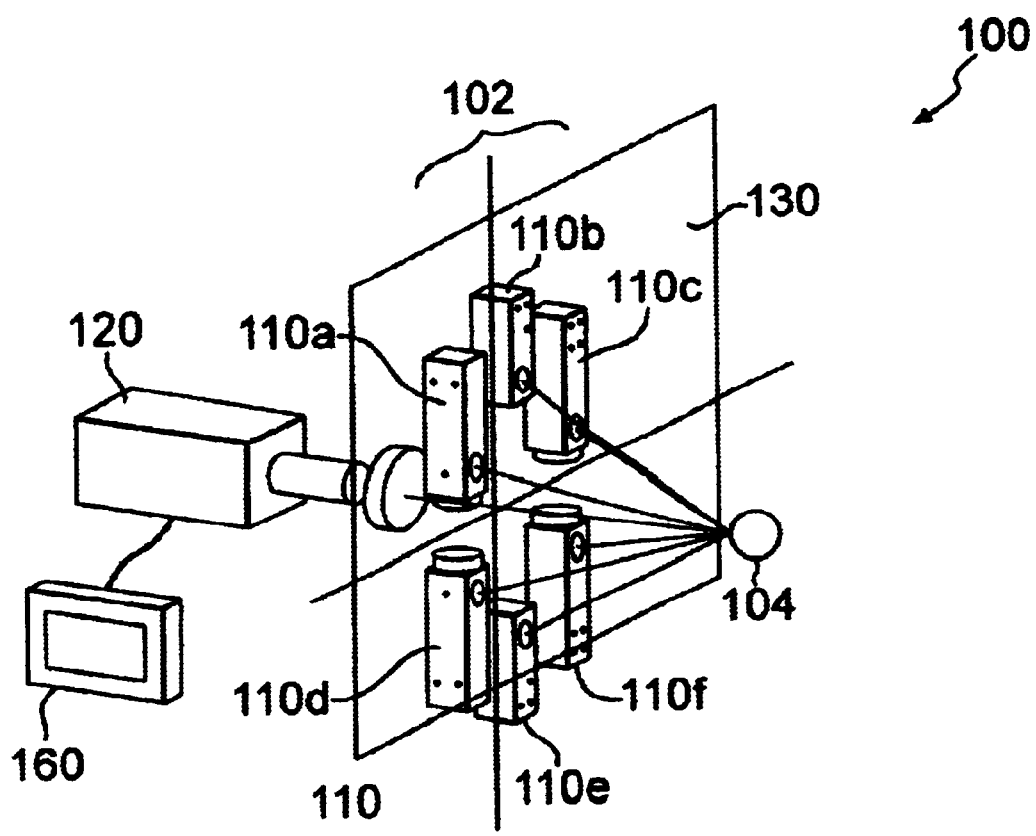
FIG. 1 is a schematic illustration of a six-light element projection component and image capture component according to an embodiment of the invention.

The embodiments of the invention will be described in detail below with reference to the accompanying figures wherein like reference numerals refer to similar references throughout.

FIG. 1 illustrates a preferred embodiment of a system 100 for monitoring the spatial position, and tracking the movement of, the corneal surface 104 of a patient's eye which by definition is spherical or quasi spherical. FIG. 1 also represents an image registration system 100 for registering multiple images of a spherical or quasi spherical object surface such as the cornea of the eye. The system and device 100 generally comprises a projection component 102 (as shown in FIG. 2), an image capture component 120 and a computing component 160 operably connected to the image capture component 120. As shown in FIGS. 2a and b, the projection component 102 includes at least one light-emitting element 110, and the projection component projects at least four spots of light 112a–d onto the (spherical or quasi-spherical) surface 104. At least two of the spots 112 will be non-coplanar on the surface as shown at 111 in FIG. 2(a). This is a necessary condition for tracking the motion and position of the surface 104 along the z direction. The at least three remaining light spots on the surface 104 are necessary to track the x-y motion of the surface.

In general, given 4 points in 3 dimensional space $(x_1,y_1,z_1)$, $(x_2,y_2,z_2)$, $(x_3,y_3,z_3)$, $(x_4,y_4,z_4)$, the equation of the sphere with those points on the surface is found by solving the following determinant:

$$\begin{vmatrix} x^2+y^2+z^2 & xyz & & 1 \\ x_1^2+y_1^2+z_1^2 & x_1y_1z_1 & & 1 \\ x_2^2+y_2^2+z_2^2 & x_2y_2z_2 & & 1 \\ x_3^2+y_3^2+z_3^2 & x_3y_3z_3 & & 1 \\ x_4^2+y_4^2+z_4^2 & x_4y_4z_4 & & 1 \end{vmatrix} = 0$$

If the determinant is found using the expansion by minors using the top row then the equation of the sphere can be written as follows:

$$(x^2+y^2+z^2)\begin{vmatrix} x_1y_1z_1 & 1 \\ x_2y_2z_2 & 1 \\ x_3y_3z_3 & 1 \\ x_4y_4z_4 & 1 \end{vmatrix}$$

$$-x\begin{vmatrix} x_1^2+y_1^2+z_1^2+y_1z_1 & 1 \\ x_2^2+y_2^2+z_2^2+y_2z_2 & 1 \\ x_3^2+y_3^2+z_3^2+y_3z_3 & 1 \\ x_4^2+y_4^2+z_4^2+y_4z_4 & 1 \end{vmatrix} + y\begin{vmatrix} x_1^2+y_1^2+z_1^2+x_1z_1 & 1 \\ x_2^2+y_2^2+z_2^2+x_2z_2 & 1 \\ x_3^2+y_3^2+z_3^2+x_3z_3 & 1 \\ x_4^2+y_4^2+z_4^2+x_4z_4 & 1 \end{vmatrix}$$

$$-z\begin{vmatrix} x_1^2+y_1^2+z_1^2+x_1y_1 & 1 \\ x_2^2+y_2^2+z_2^2+x_2y_2 & 1 \\ x_3^2+y_3^2+z_3^2+x_3y_3 & 1 \\ x_4^2+y_4^2+z_4^2+x_4y_4 & 1 \end{vmatrix} + \begin{vmatrix} x_1^2+y_1^2+z_1^2+x_1y_1z_1 \\ x_2^2+y_2^2+z_2^2+x_2y_2z_2 \\ x_3^2+y_3^2+z_3^2+x_3y_3z_3 \\ x_4^2+y_4^2+z_4^2+x_4y_4z_4 \end{vmatrix} = 0$$

In term of the minors $M_{1j}$:

$$(x^2+y^2+z^2)M_{11}-x\,M_{12}+y\,M_{13}-z\,M_{14}+M_{15}=0 \qquad 1.1$$

The general equation of a sphere with radius r centered at $(x_0,y_0,z_0)$ is $$(x-x_0)^2+(y-y_0)^2+(z-z_0)^2=r^2 \qquad 1.2$$

Rewrite equation 1.2 as $$x^2-2xx_0+x_0^2+y^2-2xx_0+y_0^2+z^2-2zz_0+z_0^2-r^2=0 \qquad 1.3$$

Rearrange 1.3 to obtain $$x^2+y^2+z^2-2xx_0-2xx_0-2zz_0+x_0^2+y_0^2+z_0^2-r^2=0 \qquad 1.4$$

Rearrange equation 1.1 to obtain $$(x^2+y^2+z^2)-x\,M_{12}/M_{11}+y\,M_{13}/M_{11}-z\,M_{14}/M_{11}+M_{15}/M_{11}=0 \qquad 1.5$$

Equating the terms from equation 1.4 and 1.5 allows one to solve for the center and radius of the sphere, namely:

$x_0=0.5\,M_{12}/M_{11}$
$y_0=0.5\,M_{13}/M_{11}$
$z_0=0.5\,M_{14}/M_{11}$
$r=(x_0^2+y_0^2+z_0^2)-(M_{15}/M_{11})$

Note that these can't be solved for $M_{11}$ equal to zero. This correspond to no quadratic terms $(x^2,y^2,z^2)$ in which case we aren't dealing with a sphere and the points are either coplanar or three are collinear.

Figure 2B:
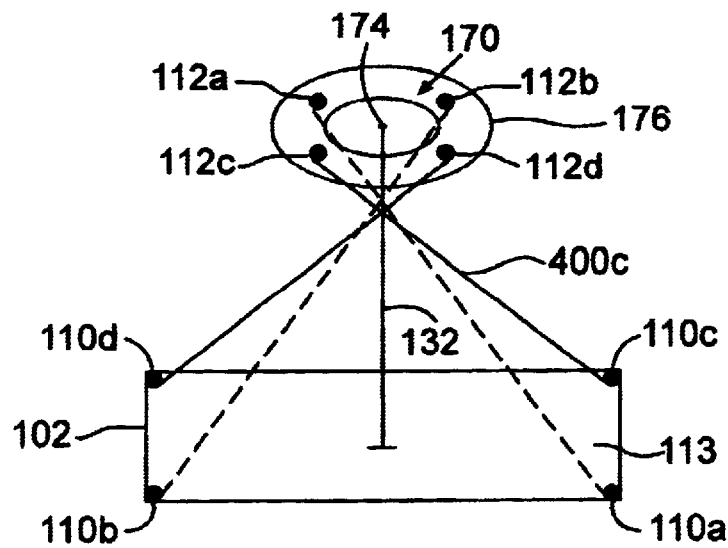
FIG. 2b is a front view illustration of a four-beam projection according to an embodiment of the invention.
Figure 6:
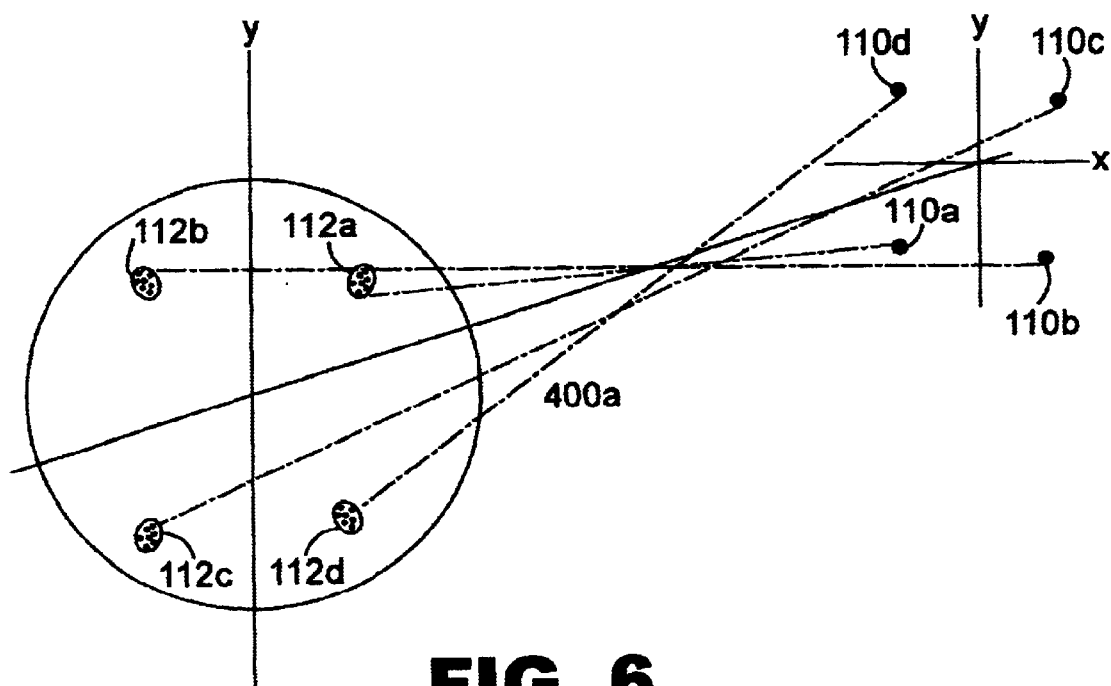
FIG. 6 is a schematic illustration of light propagation to the object surface according to an embodiment of the invention.

A generalized device embodiment according to the invention can be understood with reference to FIG. 2b. Four light-emitting elements 110a–d are in a coplanar arrangement in housing 113. The light-emitting elements 110 are preferably pin lasers that emit thin, collimated beams of light projected to the object surface 104. As shown, the object surface 104 represents a corneal surface having a center 174, an iris boundary 170, and a limbus boundary 176. As illustrated in FIG. 2b and FIG. 6, the distance between a light-emitting element 110 and its corresponding light spot 112 on the corneal surface takes an extremum path 400; that is, light-emitting element 110a in the lower right position of the housing 113 projects its beam in a path that forms a light spot 112a in the upper left part of the object surface. Likewise, the upper left light-emitting element 110d projects a beam path to form a light spot 112d in the lower right portion of the object surface. These extremum paths of maximum distance between light source and illumination spot create a light spot on the eye that is parabolic in shape due to the acute angle of the beam hitting the surface as illustrated in FIG. 6. Moreover, the preferred angular orientation of the beam paths create a diffusely reflected spot from the stromal cells of the cornea (or other surface being imaged), rather than a specular reflection, which are by their nature highly motion sensitive to any x, y, or z-movement of the object surface. Preferably, each light spot formed on the corneal surface is small relative to, for example, a constricted pupil area, and is located between about ½ to about ⅔ of the distance from a corneal center position 174 and the limbal boundary 176 of the eye, as illustrated in FIG. 2b.

In operation, the corneal surface is illuminated by the diffusely reflected, parabolic-shaped light spots, and over a diagnostic time interval, an image capture device such as a video camera captures temporally sequential images of the corneal surface and the light spots on the surface. A single image frame can be image processed by methods well known in the art to establish a spherical reference frame for the object under investigation. As each image is captured, and the spots identified, a compensation vector for each image in the temporal sequence of frames is constructed. Due to the voluntary or involuntary motion of the eye during examination, the relative positions of the light spots on the corneal surface will shift, and the new positions will be captured in each subsequent image frame. It is this relationship of the spots that allows the motion of the eye to be tracked in space. The compensation vector constructed in each image can then be used to logically shift each image frame into a uniform central frame of reference, thus compensating for any motion of the source during the video image capture process. The receiving of the images, location of the spots in each image frame, and determination of a relationship between the image spots in each image frame is accomplished by the computing component 160 and its associated software. Once a center position x, y, z, and a radius, r, of the spherical surface is determined for each image frame, each image frame can be referenced to the control image and the images registered with respect to each other resulting in a more accurate diagnostic measurement.

Figure 3:
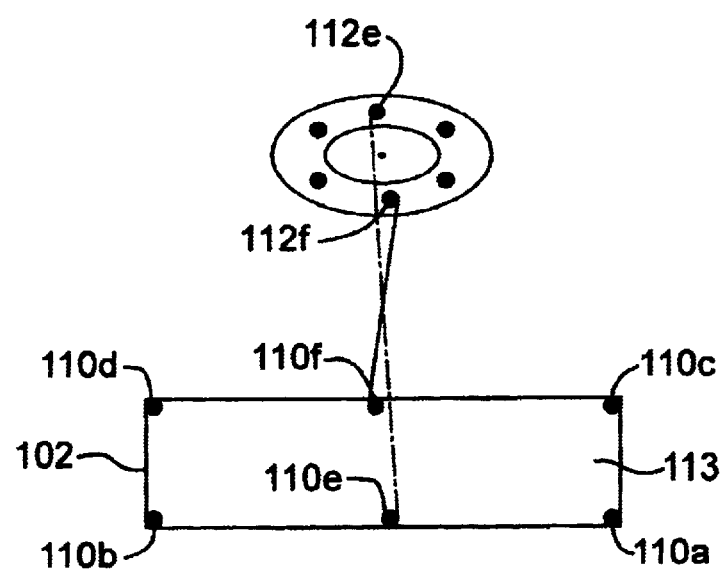
FIG. 3 is a view similar to that of FIG. 1b showing a symmetric six-beam projection according to an embodiment of the invention.
Figure 4:
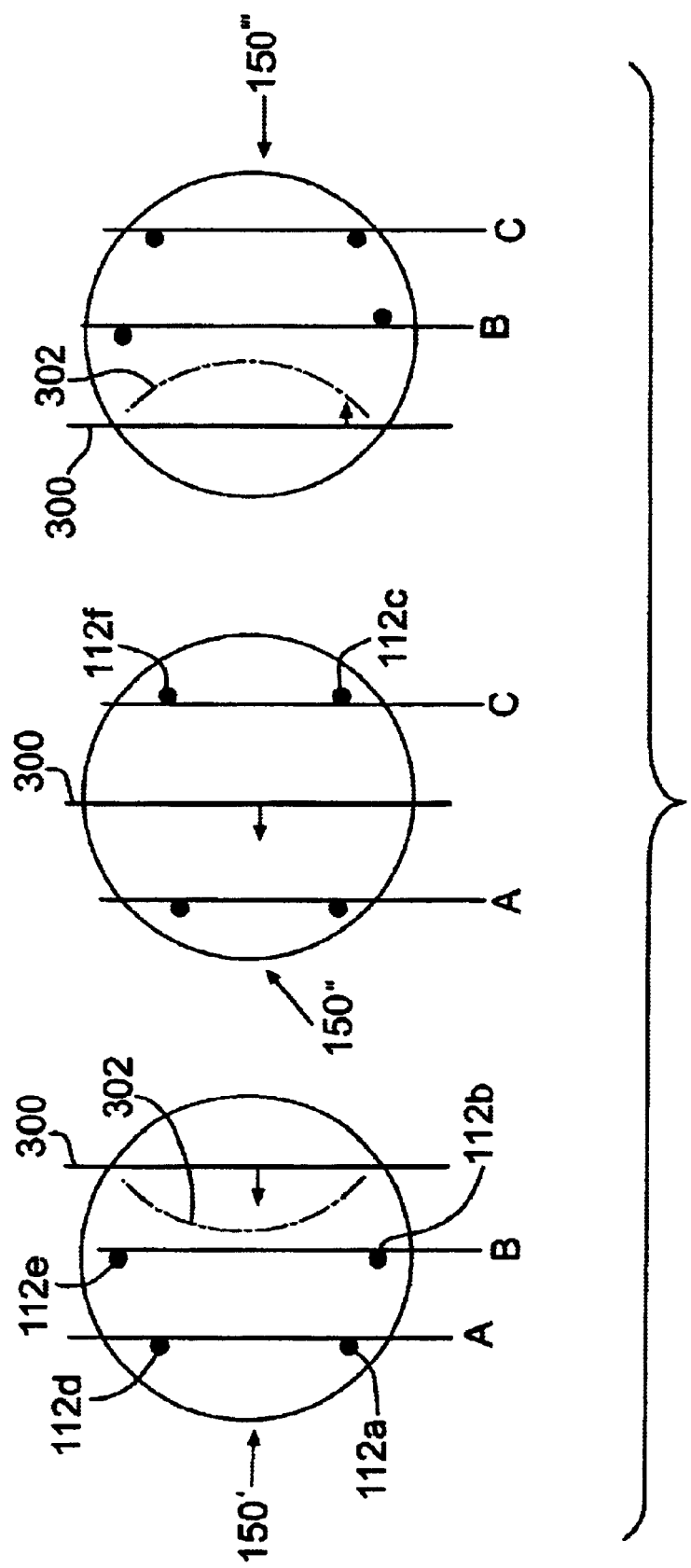
FIG. 4 is a three-sequence illustration of the banking/switching light control system as would occur in the setup illustrated in FIG. 2.

In a preferred aspect of the invention, referred to with respect to FIG. 1, the projection component 102 includes six pin lasers 110a–f which project six corresponding beams to the corneal surface 104 to form six corresponding diffuse light spots 112a–f on the corneal surface. FIG. 3 illustrates that extremum path configurations of the device, similar to the four-beam system shown in FIG. 2a, with the addition that light-emitting element 110b located in the upper center of the housing 113 projects to a lower center region 112b on the corneal surface, and light-emitting element 110e in the lower center of the housing 113 projects its beam to the upper center spot 112e on the corneal surface. As shown in FIG. 4, the light spots 112a–f are arranged as three substantially vertical pairs of light spots 112a,d; 112b,e; and 112c,f.

The preference for having six light-emitting elements is explained as follows. Topography and location of the posterior and anterior corneal surfaces represent valuable diagnostic measurements in the area of refractive surgery. Certain diagnostic devices can be used to acquire this information and include OCT devices and ultrasound devices providing certain scanning algorithms. Due to the principles of operations of these devices, it is sufficient to illuminate the corneal surface with only four light spots as described herein to monitor the position and motion of the eye during the diagnostic measurement. There are drawbacks with the use of these types of instruments that are appreciated by those skilled in the art, which are not germane to the invention and therefore need not be discussed in further detail. An alternative measurement methodology is embodied in devices that use what is referred to herein as a competing light source to acquire their measurement data. For example, the Orbscan® topographical mapping system (Bausch & Lomb Incorporated, Rochester, N.Y.) utilizes a slit of light produced by a laser which is scanned back and forth over the eye and is reflected off of various surfaces in the eye. This is illustrated diagrammatically in FIG. 4 in which three sequential images 150', 150", and 150'" are shown. Beginning with the left most image, the corneal surface 104 is shown with six light spots 112 represented as banks A, B, and C. Bank A consists of a pair of light spots 112a, 112d that are vertically co-aligned as shown. Similarly, Bank B consists of light spot pair 112b, 112e and Bank C consists of light spot pair 112c, 112f. A laser light slit 300 is projected onto the corneal surface in FIG. 150' beginning at the right side of the eye. The laser slit is reflected off of the anterior corneal surface (behind line 300) and is also reflected off of the posterior corneal surface as shown as curved line 302. As the laser slit is scanned over the corneal surface from right to left, it can be seen that at some point the laser slit 300 will co-align with the vertically oriented light spots 112c, 112f of Bank C. At some later time as illustrated by frame 150", the laser slit 300 will obscure, or compete with, Bank B comprising light spots 112b, 112e. As the laser slit completes its scan as shown in 150'", the illumination spots of Bank A are obscured. In order to compensate for the competing light source 300, a bank switching control (not shown) is incorporated into the device such that any bank or pair of light spots can be switched off when they become obscured by the competing light source. In this manner, there are always at least four light spots illuminating the corneal surface during the entire video image capture duration.

Figure 5:
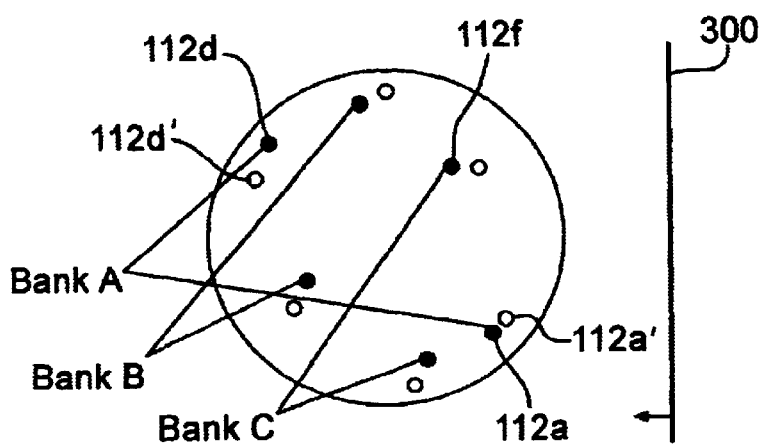
FIG. 5 is an illustration similar to that of FIG. 3 showing an alternative arrangement of six light spots according to an embodiment of the invention.

An alternative preferred aspect of this embodiment is shown with respect to FIG. 5. In FIG. 5, no two light spots nor any pair (bank) of light spots is in vertical co-alignment. Thus, when the laser slit 300 moving from right to left first obscures light spot 112a, Bank A can be deactivated such that the four light spots from Banks B and C continue to illuminate the corneal surface. Likewise, the next obscured light spot will be 112f and when it is obscured by the competing laser slit 300, Bank C (112f,c) can be turned off leaving Banks A and B to illuminate the eye.

In an alternative aspect, the angular orientation of each propagation path from the light-emitting element to its corresponding light spot on the corneal surface could be different from every other propagation orientation to illuminate the corneal surface in an irregular manner.

While various advantageous embodiments have been chosen to illustrate the invention, it will be understood by those skilled in the art that changes and modifications can be made therein without departing from the scope of the invention as defined in the appended claims.

We claim:

1. A device for monitoring the spatial position of, and tracking the movement of, an object having a spherical or quasi-spherical surface, comprising:

a projection component including at least one light emitting element, wherein said projection component projects at least four spots of light onto the surface, at least two of the spots being non-coplanar on the surface;

an image capture component adapted to capture a temporal plurality of image frames of the at least four spots of light on the surface, wherein at least one of the image frames is a control image; and a computing component operably connected to the image capture component, said computing component adapted to (i) receive the images from the image capture component, (ii) locate each spot in each image frame, and (iii) determine a relationship between the imaged spots in each image frame.

2. The device of claim 1, wherein each imaged spot of light on the surface is defined with respect to each of an x-axis, a y-axis, and a z-axis.

3. The device of claim 1, wherein the projection component includes at least four light emitting elements, wherein said projection component projects four spots of light onto the surface.

4. The device of claim 3, wherein the light emitting elements are lasers.

5. The device of claim 3, further comprising a bank-switching system for controlling any selected pair of said at least four light emitting elements.

6. The device of claim 1, wherein the projection component includes six light emitting elements, wherein said projection component projects at least four identifiable spots of light onto the surface.

7. The device of claim 6, wherein the light emitting elements are lasers.

8. The device of claim 6, further comprising a bank-switching system for controlling any selected pair of said six light emitting elements.

9. The device of claim 1, wherein the at least one light emitting element is an incandescent light source.

10. The device of claim 1, wherein the at least one light emitting element is a laser.

11. The device of claim 1, wherein the at least four spots of light are projected from a plane that is normal to a reference axis of the surface.

12. The device of claim 1, wherein the at least four spots of light are projected onto a corneal surface and are projected from a plane that is normal to an optical axis of the corneal surface.

13. The device of claim 12, wherein said at least four spots of light projected onto the corneal surface have a surface area that is small relative to an iris area of the corneal surface, and further wherein each light spot is projected onto the corneal surface in a beam having an origin that provides a maximum distance from the origin to the corneal surface.

14. The device of claim 13, wherein each light spot on the corneal surface is located at a distance between about ½ to ⅔ of the distance from a center of the corneal surface to a limbal boundary of the cornea.

15. The device of claim 1, wherein each light spot on the corneal surface has a parabolic surface shape.

16. The device of claim 1, wherein the image capture component is a camera.

17. The device of claim 1, wherein said computing component is further adapted to register each image with one another in such a manner that each spherical surface in each image frame is concentric about a reference center.

18. The device of claim 1, wherein said device is itself a component of a corneal topography device.

19. An image registration system for registering multiple images of a moving spherical or quasi-spherical object surface, comprising:

at least four laser spot devices in fixed, relative positions for illuminating with at least four corresponding light spots the spherical or quasi-spherical object surface at at least four distinct locations, wherein at least one location is non-coplanar with respect to the at least three other locations;

an image detector for capturing a temporal plurality of image frames of the spherical or quasi-spherical object surface and the at least four illuminated locations;

a computing component including software, operably connected to the image detector, for determining a center position, $(x_0, y_0, z_0)$, and a radius, r, of the spherical or quasi-spherical object surface based on the captured image frames, and for registering each of the plurality of image frames relative to the other of the plurality of the image frames based upon a change in position of each of the at least four locations detected on the captured images.

20. The system of claim 19, further comprising a housing for maintaining the at least four laser spot devices in fixed, relative positions.

21. The system of claim 19, wherein a distance between each laser spot device and its corresponding illuminating location is a maximum distance.

22. The system of claim 19, comprising six laser spot devices in fixed, relative positions for illuminating with six corresponding light spots the spherical or quasi-spherical object surface at six distinct locations, wherein at least one location is non-coplanar with respect to the five other locations.

23. The system of claim 22, wherein none of the six distinct locations are collinear in a horizontal or a vertical direction.

24. The system of claim 22, wherein the laser spot devices and associated six light spots are grouped into three banked-pairs.

25. The system of claim 24, further comprising a bank-switching system for controlling any selected pair of said laser spot devices.

26. The system of claim 25, wherein any two selected pair of laser spot devices illuminate the surface during every image frame capture.

27. The system of claim 19, wherein each light spot is a diffuse reflection from the object surface.

28. The system of claim 19, wherein none of the at least four distinct locations are collinear in a horizontal or a vertical direction.

29. The system of claim 19, wherein each laser spot device projects its respective light spot along a path having an angular orientation to a reference axis of the object surface that is different than any other path orientation.

30. The system of claim 19, wherein the moving spherical or quasi-spherical object surface is a corneal surface of a patient's eye.

31. The system of claim 19, wherein the system is itself a component of an ophthalmic diagnostic system.

32. The system of claim 31, wherein the ophthalmic diagnostic system is a corneal topography measuring system.

33. The system of claim 32, wherein the corneal topography measuring system is a slit-scanning system.

* * * * *